United States Patent
Centanni

(10) Patent No.: US 7,186,373 B2
(45) Date of Patent: Mar. 6, 2007

(54) VISUAL DETECTOR FOR VAPORIZED HYDROGEN PEROXIDE

(75) Inventor: Michael A. Centanni, Parma, OH (US)

(73) Assignee: Steris Inc., Temecula, CA (US)

( * ) Notice: Subject to any disclaimer, the term of this patent is extended or adjusted under 35 U.S.C. 154(b) by 436 days.

(21) Appl. No.: 10/624,770

(22) Filed: Jul. 22, 2003

(65) Prior Publication Data

US 2005/0019206 A1    Jan. 27, 2005

(51) Int. Cl.
A61L 2/24    (2006.01)

(52) U.S. Cl. ............ 422/3; 422/1; 422/28; 422/119; 422/292; 436/1

(58) Field of Classification Search ............ 422/1, 422/3, 28, 119, 292; 436/1
See application file for complete search history.

(56) References Cited

U.S. PATENT DOCUMENTS

| | | | |
|---|---|---|---|
| 2,232,622 A * | 2/1941 | Moses et al. ............ 422/87 |
| 2,741,544 A * | 4/1956 | Chalkin et al. ............ 422/91 |
| 4,046,577 A | 9/1977 | Muzyczko et al. ......... 96/115 |
| 4,155,895 A | 5/1979 | Rohowetz et al. ......... 260/33.4 |
| 4,205,043 A * | 5/1980 | Esch et al. .............. 422/56 |
| 4,643,876 A | 2/1987 | Jacobs et al. ............ 422/23 |
| 4,756,758 A | 7/1988 | Lent et al. .............. 106/22 |
| 4,756,882 A | 7/1988 | Jacobs et al. ............ 422/23 |
| 4,843,867 A | 7/1989 | Cummings ............... 73/23 |
| 4,863,627 A | 9/1989 | Davies et al. ............ 424/10.32 |
| 4,956,145 A | 9/1990 | Cummings et al. ........ 422/28 |
| 5,053,339 A | 10/1991 | Patel .................... 463/2 |
| 5,087,659 A | 2/1992 | Fujisawa et al. .......... 524/594 |
| 5,139,957 A | 8/1992 | Grack ................... 436/135 |
| 5,173,258 A | 12/1992 | Childers ................ 422/27 |
| 5,352,282 A | 10/1994 | Miller .................. 106/22 |
| 5,420,000 A | 5/1995 | Patel et al. ............. 430/332 |
| 5,445,792 A | 8/1995 | Rickloff et al. .......... 422/28 |
| 5,482,684 A | 1/1996 | Martens et al. .......... 422/119 |
| 5,518,927 A | 5/1996 | Malchesky et al. ........ 436/1 |
| 5,620,656 A | 4/1997 | Wensky et al. .......... 422/28 |
| 5,770,150 A * | 6/1998 | Thornton et al. ......... 422/61 |
| 5,788,925 A | 8/1998 | Pai et al. ............... 422/3 |
| 5,789,175 A * | 8/1998 | Priest .................. 436/1 |
| 5,872,004 A | 2/1999 | Bolsen ................. 435/287.4 |
| 5,942,193 A | 8/1999 | Bolsen ................. 422/119 |
| 5,942,438 A | 8/1999 | Antonoplos et al. ....... 436/1 |
| 5,955,025 A | 9/1999 | Barrett ................. 422/28 |
| 5,990,199 A | 11/1999 | Bealing et al. .......... 523/161 |
| 6,063,631 A | 5/2000 | Ignacio ................. 436/1 |
| 6,087,089 A * | 7/2000 | Wu ..................... 435/4 |
| 6,156,267 A | 12/2000 | Pai et al. ............... 422/3 |
| 6,218,189 B1 | 4/2001 | Antonoplos et al. ....... 436/1 |
| 6,238,623 B1 | 5/2001 | Amhof et al. ........... 422/58 |
| 6,267,242 B1 | 7/2001 | Nagata et al. .......... 206/459.1 |
| 6,287,518 B1 | 9/2001 | Ignacio et al. .......... 422/86 |
| 6,346,417 B1 | 2/2002 | Ignacio et al. .......... 436/1 |
| 6,410,338 B1 | 6/2002 | Lippold et al. .......... 436/166 |
| 6,440,744 B1 | 8/2002 | Ignacio et al. .......... 436/1 |
| 6,488,890 B1 * | 12/2002 | Kirckof ................ 422/56 |
| 6,551,555 B2 | 4/2003 | Antonoplos et al. ....... 422/58 |
| 6,790,411 B1 | 9/2004 | Read ................... 422/28 |
| 2002/0151084 A1 | 10/2002 | Lippold et al. .......... 436/163 |
| 2004/0265170 A1 | 12/2004 | Read ................... 422/56 |

FOREIGN PATENT DOCUMENTS

| | | |
|---|---|---|
| DE | 273 775 | 11/1989 |
| DE | 273 776 | 11/1989 |
| EP | 0 914 833 | 12/1999 |
| EP | 1 052 507 | 11/2000 |
| JP | 49-46440 | 12/1974 |
| JP | 11-178904 | 7/1999 |
| WO | WO 92/22806 | 12/1992 |
| WO | WO 96/33242 | 10/1996 |
| WO | WO 98/46279 | 10/1998 |
| WO | WO 98/46994 | 10/1998 |
| WO | WO 98/52621 | 11/1998 |
| WO | WO 98/58683 | 12/1998 |
| WO | WO 00/61200 | 10/2000 |
| WO | WO 01/40792 | 6/2001 |

OTHER PUBLICATIONS

Bishop, "Chapter 8B: Oxidation-Reduction Indicators of High Formal Potential," Indicators, Bishop, ed., Pergamon Press Ltd., Braunschweig, Germany, Title Page, publication page, table of contents, and pp. 531-684 (1972).

(Continued)

Primary Examiner—Krisanne Jastrzab
(74) Attorney, Agent, or Firm—Kusner & Jaffe; Michael A. Centanni

(57) ABSTRACT

A method and apparatus for sensing the concentration of a gaseous sterilant in a sealable enclosure. An indicator is provided that has a chemistry such that the indicator changes color when exposed to vaporized hydrogen peroxide (VHP). The chemistry is adapted to react when exposed to a specific minimum concentration of vaporized hydrogen peroxide for a specific minimum period of time. In this manner, it can be visually determined whether articles (e.g., medical instruments and like devices) located within the sealable enclosure have been exposed to a minimum threshold of vaporized hydrogen peroxide.

15 Claims, 2 Drawing Sheets

OTHER PUBLICATIONS

Lillie et al., "Ch. 2: The General Nature of Dyes and Their Classification," H.J. Conn's Biological Stains, a Handbook On the Nature and Uses of the Dyes Employed in the Biological Laboratory, 9.sup.th ed., The Williams & Wilkins Company, available from the Sigma Chemical Company, St. Louis, Mo., Title page, publication page, publication page, and pp. 19-32, 382-384, and 429-430 (1977).

Article entitled: "*Hydrogen Peroxide Iodine Clock: Oxidation of Potassium Iodide by Hydrogen Peroxide,*" Shakhashiri, Chemical Demonstrations: A Handbook for Teachers of Chemistry, 1992, vol. 4, pp. 37-43.

Article entitled: "*Kinetics: The Reaction of I with $H_2O_2$ Using Initial Rate Methods,*" Berka et al.

Article entitled: "*Kinetics: The Reaction of I with $H_2O_2$ Using Pseudo-Order Methods (Version 1),*" Berka et al.

Article entitled: "*Kinetics: The Reaction of I with $H_2O_2$ (Version 2),*" Berka et al.

\* cited by examiner

VISUAL DETECTOR FOR VAPORIZED HYDROGEN PEROXIDE

FIELD OF THE INVENTION

The present invention relates generally to decontamination systems, and more particularly to a method and apparatus for sensing the concentration of a gaseous sterilant in a sealable enclosure.

BACKGROUND OF THE INVENTION

Conventional, gaseous sterilization systems typically flow a vaporized sterilant through a sealable sterilization chamber. In such systems, it is important to maintain a desired concentration of the gaseous sterilant in the sterilization chamber during a sterilization cycle to effect deactivation of harmful biocontamination, such as viruses, bacteria and prions.

When the sterilant of choice is vapor phase hydrogen peroxide, which is typically generated from an aqueous solution of liquid hydrogen peroxide, it is difficult to determine the concentration of vaporized hydrogen peroxide in the sterilization chamber.

The present invention provides a method and apparatus for providing a visual indication of the presence of a sterilant in a sterilization chamber.

SUMMARY OF THE INVENTION

In accordance with a preferred embodiment of the present invention, there is provided in an apparatus having a chamber for decontaminating articles by exposing said articles to vaporized hydrogen peroxide (VHP), a system for visually verifying a minimum concentration of vaporized hydrogen peroxide (VHP) in said chamber, said system comprising: (a) a generally continuous web indicator that changes color when exposed to vaporized hydrogen peroxide (VHP), said web indicator having a specific reaction rate based upon a concentration of vaporized hydrogen peroxide (VHP) exposed thereto; and (b) a device for conveying said web indicator through said chamber during a decontamination cycle at a predetermined rate, wherein a portion of said web indicator is continuously exposed to vaporized hydrogen peroxide (VHP) in said chamber for a specific period of time, said rate and period of exposure being set to cause said web indicator to change color if a predetermined concentration of vaporized hydrogen peroxide (VHP) is present in said chamber.

In accordance with another aspect of the present invention, there is provided in an apparatus having a chamber for decontaminating articles by exposing said articles to vaporized hydrogen peroxide (VHP), a system for visually verifying a minimum concentration of vaporized hydrogen peroxide (VHP) in said chamber, said system comprising: an indicator that changes color when exposed to vaporized hydrogen peroxide (VHP), said indicator having a specific reaction rate based upon a concentration of vaporized hydrogen peroxide (VHP) exposed thereto.

In accordance with still another aspect of the present invention, there is provided in an apparatus having a chamber for decontaminating articles by exposing said articles to vaporized hydrogen peroxide (VHP), a method for visually verifying a minimum concentration of vaporized hydrogen peroxide (VHP) in said chamber, said method comprising the steps of: (a) advancing a generally continuous web indicator through said chamber, and (b) exposing said web indicator to a concentration of vaporized hydrogen peroxide, said web indicator changing color when exposed to vaporized hydrogen peroxide (VHP), wherein said web indicator has a specific reaction rate based upon the concentration of vaporized hydrogen peroxide (VHP) exposed thereto.

In accordance with still another aspect of the present invention, there is provided in an apparatus having a chamber for decontaminating articles by exposing said articles to vaporized hydrogen peroxide (VHP), a system for visually verifying a minimum concentration of vaporized hydrogen peroxide (VHP) in said chamber, said system comprising: (a) introducing vaporized hydrogen peroxide into said chamber; and (b) exposing an indicator to a concentration of vaporized hydrogen peroxide, said indicator changing color when exposed to vaporized hydrogen peroxide (VHP), wherein said indicator has a specific reaction rate based upon the concentration of vaporized hydrogen peroxide (VHP) exposed thereto.

An advantage of the present invention is the provision of a method and apparatus for testing a concentration level of vaporized hydrogen peroxide (VHP) in a decontamination chamber.

Another advantage of the present invention is the provision of a method and apparatus that provides a visual record of the history of exposure of instruments to VHP in a decontamination system.

Another advantage of the present invention is the provision of a method and apparatus that permits a visual determination of whether medical instruments and like devices have been exposed to a minimum threshold of VHP.

These and other objects will become apparent from the following description of a preferred embodiment taken together with the accompanying drawings and the appended claims.

BRIEF DESCRIPTION OF THE DRAWINGS

The invention may take physical form in certain parts and arrangement of parts, a preferred embodiment of which will be described in detail in the specification and illustrated in the accompanying drawings which form a part hereof, and wherein.

DETAILED DESCRIPTION OF PREFERRED EMBODIMENT

Figure 1:
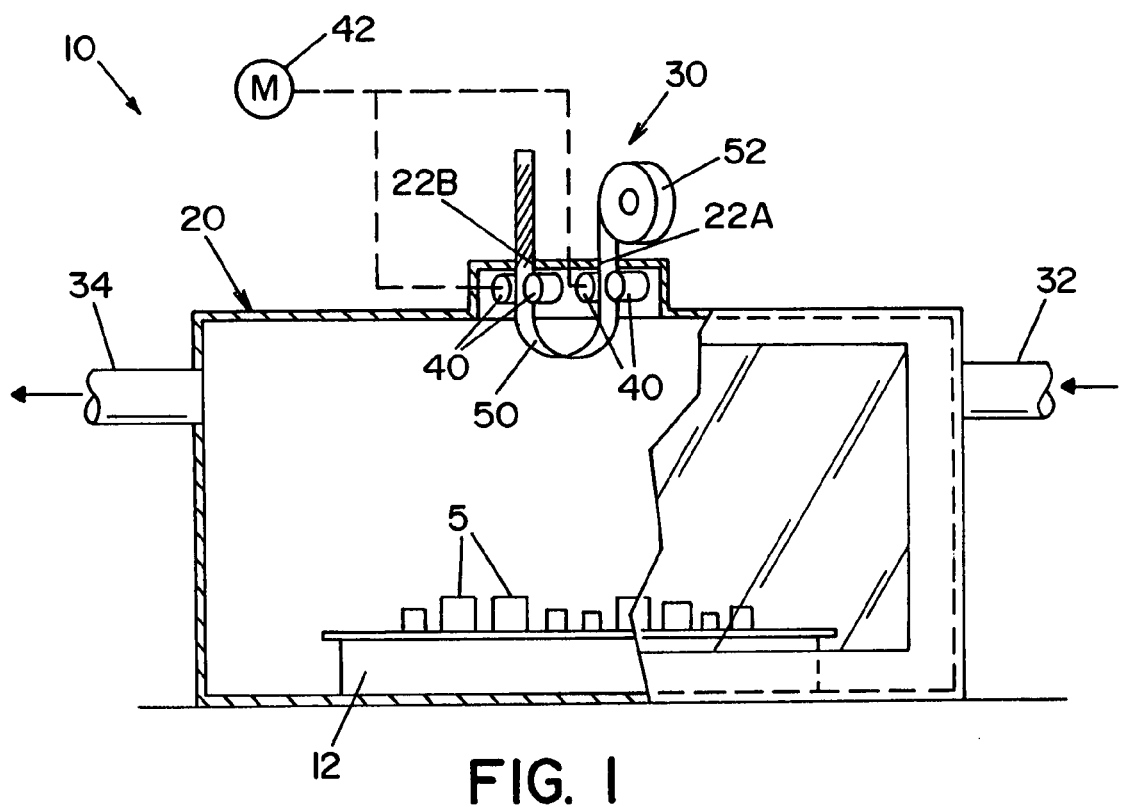
FIG. 1 is a partially-sectioned, elevational view of a decontamination system including a treatment chamber and a visual detector system, illustrating a first embodiment of the present invention.

Broadly stated, the present invention is comprised of an indicator having a chemistry such that the indicator changes color when exposed to vaporized hydrogen peroxide (VHP). In one embodiment of the present invention, the indicator is generally comprised of a continuous strip that may be continuously or intermittently conveyed through a treatment chamber during a decontamination (e.g., sterilization) cycle, wherein portions of the indicator are exposed to the atmosphere within the treatment chamber for a predetermined period of time during a decontamination cycle. In another embodiment of the present invention, the indicator may be formed as a stationary strip disposed within a treatment chamber for exposure to the atmosphere within the treatment chamber during a decontamination cycle.

The foregoing embodiments of the present invention are based upon the kinetics of the chemistry of the indicator, i.e., the rate at which (and the path by which) a chemical reaction occurs. In this respect, each embodiment of the indicator has a chemistry adapted to react when exposed to a specific minimum concentration of vaporized hydrogen peroxide (VHP) for a specific minimum period of time. In this respect, the chemistry of an indicator is designed to produce a color change when a desired concentration exists for a set period of time. Such conditions drive a chemical reaction that provides a color change indicative that the minimum desired concentration existed for the desired time period.

When the sterilant of choice is vaporized hydrogen peroxide (VHP), which is commonly generated from an aqueous solution of liquid hydrogen peroxide, it is typically desired to maintain a minimum concentration of vaporized hydrogen peroxide (VHP) in a treatment chamber, as it is the vaporized hydrogen peroxide (VHP) that is the active agent in sterilizing articles (e.g., instruments) within the chamber. Typically, it is desirable to maintain a minimum vapor concentration of at least 500 to 1500 ppm through a decontamination cycle. The chemistry of an indicator is established to cause a color change if at least the minimum concentration of VHP is maintained for a desired period of time.

The concentration of vaporized hydrogen peroxide (VHP) present in a treatment chamber is indicative of the number of VHP molecules available to drive a chemical reaction with the indicator. In other words, the higher the concentration of vaporized hydrogen peroxide (VHP), the larger the number of molecules available to interact with the chemistry of the indicator.

Referring now to a suitable chemistry for an indicator for exposure to vaporized hydrogen peroxide (VHP), an indicator includes chemistry having an iodide ion ($I^-$), a thiosulfate ($S_2O_3^{2-}$) ion and starch. When this chemistry is exposed to vaporized hydrogen peroxide ($H_2O_2$), the vapor phase hydrogen peroxide ($H_2O_2$) reacts with iodide ion ($I^-$) and hydronium ion ($H^+$) to give a triodide ion ($I_3^-$) and water.

$$H_2O_2 + 3I^- + 2H^+ \rightarrow I_3^- + 2H_2O \qquad (1)$$

The thiosulfate ($S_2O_3^{2-}$) reacts quantitatively with the triodide ion ($I_3^-$) and water according to the following:

$$I_3^- + 2S_2O_3^{2-} \rightarrow 3I^- + S_4O_6^{2-} \qquad (2)$$

This latter reaction occurs very rapidly relative to the foregoing reaction. Thus, so long as $S_2O_3^{2-}$ is present on the indicator, the triodide ion ($I_3^-$) produced by reaction (1) will be converted back to iodide ion ($I^-$) by reaction (2). Since reaction (2) occurs very rapidly relative to reaction (1), iodide ions ($I^-$) will continue to be produced and exist until the thiosulfate is gone. At that point, triodide ions ($I_3^-$) will accumulate and immediately produce a blue color.

Thus, with the foregoing chemistry, the amount of thiosulfate on the indicator will determine how much vapor phase hydrogen peroxide can react with the thiosulfate within a certain time interval before the color change occurs. By determining the desired concentration and the desired VHP exposure time, a concentration of thiosulfate for the indicator can be established, wherein the indicator will change color only when a minimum desired concentration of VHP is present for a minimum desired exposure time.

Referring now to the drawings wherein the showings are for the purpose of illustrating the preferred embodiment of the invention only, and not for the purpose of limiting same, FIG. 1 shows a decontamination system 10 including a treatment chamber 20 and a visual detector system 30, illustrating a first embodiment of the present invention. Treatment chamber 20 includes an inlet 32 and an outlet 34 for passing vaporized hydrogen peroxide therethrough. The vaporized hydrogen peroxide may be produced in a vaporization chamber (not shown) from an aqueous solution of liquid hydrogen peroxide. In the illustrated embodiment, articles 5 to be treated with vaporized hydrogen peroxide are located within chamber 20 on a support member 12.

Visual detector system 30 is generally comprised of a media advancement means and an indicator 50. In the illustrated embodiment, indicator 50 takes the form of a continuous web arranged on a roll 52. Indicator 50 includes a media (including, but not limited to, paper, a polymer and the like) coated with the indicator chemistry discussed above. In the illustrated embodiment, the media advancement means is comprised of two pairs of rollers 40 driven by a motor 42. A control unit (not shown) controls the operation (i.e., rotation) of motor 42, and thus the advancement of indicator 50. Rollers 40 are located inside chamber 20, and advance indicator 50 through treatment chamber 20. As illustrated in FIG. 1, a portion of indicator 50 enters chamber 20 through a first slot 22A in a wall of chamber 20, is threaded between the two pairs of rollers 40, and exits chamber 20 through a second slot 22B in a wall of chamber 20.

In a preferred embodiment, the generally continuous indicator 50 is conveyed through treatment chamber 20 to allow only a section (i.e., length) of indicator 50 to be exposed to the vaporized hydrogen peroxide (VHP) in chamber 20, for only a portion of the total decontamination cycle time. The chemistry on indicator 50 is designed to change color when a section of indicator 50 within chamber 20 is exposed to the desired concentration of vaporized hydrogen peroxide (VHP).

For example, indicator 50 may be dimensioned to be conveyed such that a given section of indicator 50 is within chamber 20 for only one-fifth (⅕) of the total decontamination cycle, and thus exposed to the vaporized hydrogen peroxide (VHP) within chamber 20 for only one-fifth (⅕) of the total decontamination cycle. If the section of indicator 50 within chamber 20 changes color, it is indicative of the vaporized hydrogen peroxide (VHP) within chamber 20 being at a desired concentration level, for that portion of the cycle time. In this manner, one can visually confirm that a minimum desired concentration level of vaporized hydrogen peroxide (VHP) has been maintained within chamber 20 for this portion of the exposure time. In other words, indicator 50 provides an indication that the vaporized hydrogen peroxide (VHP) concentration within chamber 20 for a given interval of the entire decontamination cycle is at a minimum desired concentration level. It should be appreciated that indicator 50 may be conveyed through chamber 20 continuously (i.e., continuously advanced through chamber 20) or intermittently (i.e., periodically advanced through chamber 20).

Figure 2:
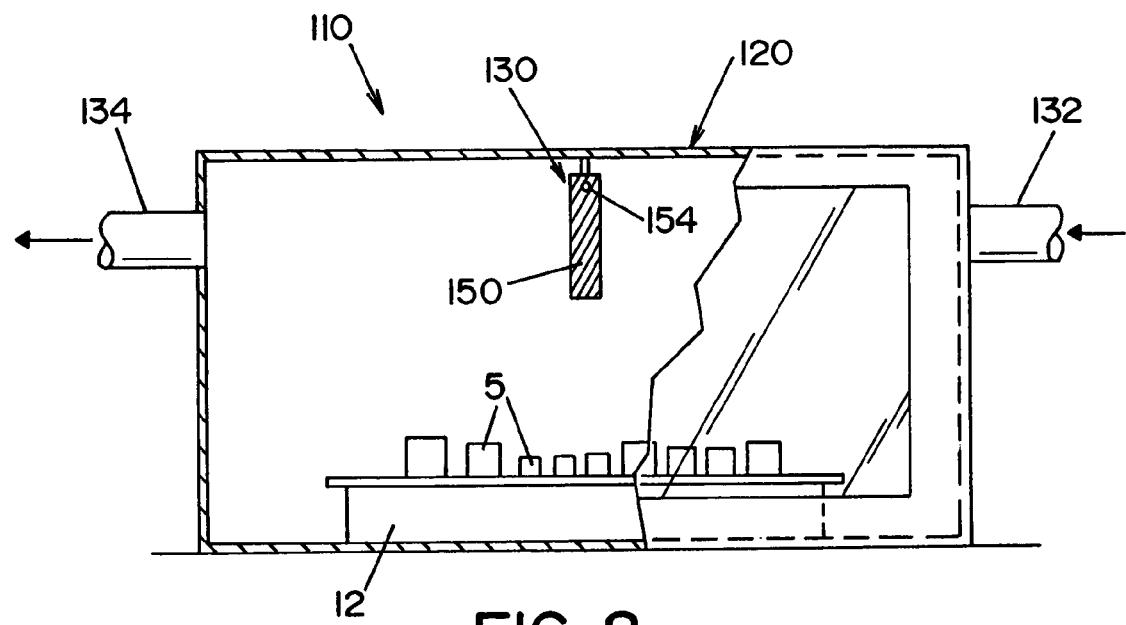
FIG. 2 is a partially-sectioned, elevational view of a decontamination system including a treatment chamber and a visual detector system, illustrating a second embodiment of the present invention.

Referring now to FIG. 2, an alternative embodiment of the present invention will be described. Decontamination system 110 includes a treatment chamber 120 and a visual detector system 130, illustrating a second embodiment of the present invention. Treatment chamber 120 includes an inlet 132 and an outlet 134 for passing vaporized hydrogen peroxide therethrough. The vaporized hydrogen peroxide may be produced in a vaporization chamber (not shown) from an aqueous solution of liquid hydrogen peroxide. In the illustrated embodiment, articles 5 to be treated with vaporized hydrogen peroxide are located within chamber 120 on a support member 12.

Visual detector system 130 is generally comprised of an indicator 150 in the form of a strip. Indicator 150 includes a media (including, but not limited to, paper, a polymer, and the like) coated with the indicator chemistry discussed above. In a preferred embodiment, a hole 154 is formed in indicator 150 to suspend indicator 150 from the top wall of chamber 120, as shown in FIG. 2. The chemistry of indicator 150 is created to cause the strip to change color indicating that the strip has been exposed to a desired average concentration of vaporized hydrogen peroxide (VHP) throughout a decontamination cycle. For example, if indicator 150 is to be disposed within treatment chamber 120 for an entire decontamination cycle, the chemistry of indicator 150 is operable to change color if the strip is exposed to a minimum average concentration of vaporized hydrogen peroxide (VHP) for the decontamination period.

Figure 3:
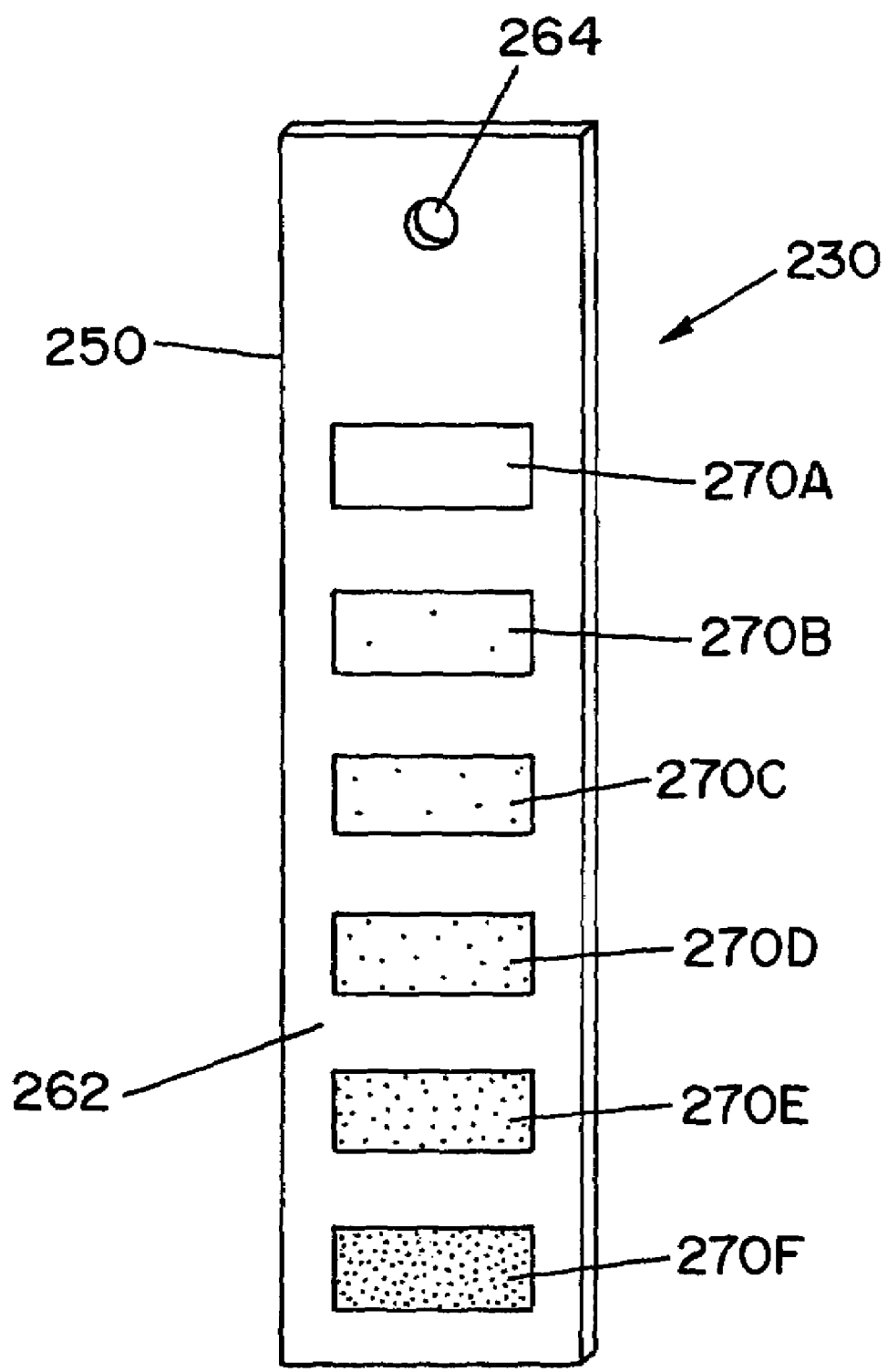
FIG. 3 is a perspective view of a visual detector system comprised of an indicator having a plurality of indicator panels, illustrating still another embodiment of the present invention.

Still another embodiment of a visual detector system is shown in FIG. 3. Visual detector system 230 is generally comprised of an indicator 250 taking the form of a strip. The strip is formed of a support media 262 for supporting a plurality of individual indicator panels 270A–270F. By way of example, and not limitation, support media 262 may be formed of paper, a polymer and the like. In the illustrated embodiment, a hole 264 is formed in support media 262 of indicator 250 to facilitate suspension of indicator 250 from the top wall of chamber 120, in the same manner as indicator 150 is suspended in FIG. 2.

In accordance with a preferred embodiment, indicator panels 270A–270F are comprised of a media (including, but not limited to, paper, polymer and the like) coated with the indicator chemistry discussed above. Alternatively, indicator panels 270A–270F may take the form of regions of support media 262 coated with the abovementioned indicator chemistry.

Indicator panels 270A–270F form an incremental gradient indicator. In this regard, each indicator panel 270A–270F has a respective chemistry that causes each indicator panel 270A–270F to change color, after a different exposure time to a desired average concentration of vaporized hydrogen peroxide (VHP), throughout a decontamination cycle. The amount of thiosulfate on the indicator panel 270A–270F will determine how much vapor phase hydrogen peroxide can react with the thiosulfate within a certain time interval before the color change occurs. Accordingly, the less thiosulfate on the indicator panel, the faster a color change will be observed when the indicator panel is exposed to vapor phase hydrogen peroxide. For example, in the illustrated embodiment, indicator panel 270A has a respective chemistry that causes it to change color after $\Delta t$ minutes of exposure to a desired average concentration of vaporized hydrogen peroxide. Likewise, indicator panels 270B, 270C, 270D, 270E, and 270F have respective chemistries that causes them to respectively change color after $2\Delta t$, $3\Delta t$, $4\Delta t$, $5\Delta t$, and $6\Delta t$ minutes of exposure to a desired average concentration of vaporized hydrogen peroxide.

The foregoing description is a specific embodiment of the present invention. It should be appreciated that this embodiment is described for purposes of illustration only, and that numerous alterations and modifications may be practiced by those skilled in the art without departing from the spirit and scope of the invention. It is intended that all such modifications and alterations be included insofar as they come within the scope of the invention as claimed or the equivalents thereof.

Having described the invention, the following is claimed:

1. In an apparatus having a chamber for decontaminating articles by exposing said articles to vaporized hydrogen peroxide (VHP), a system for visually verifying a minimum concentration of vaporized hydrogen peroxide (VHP) in said chamber, said system comprising:

a plurality of indicator panels having a chemistry thereon comprising iodide and thiosulfate, each of said plurality of indicator panels having a different amount of thiosulfate thereon, whereby each of said plurality of indicator panels undergoes a single permanent color change after a different exposure time to said minimum concentration of vaporized hydrogen peroxide, said single permanent color change produced by depletion of the thiosutfate and accumulation of triodide ions ($I_3^-$).

2. A system according to claim 1, wherein said chemistry includes an iodide ion ($I^{31}$), a thiosulfate ($S_2O_3^{2-}$) ion and starch.

3. A system according to claim 1, wherein said chemistry is coated onto a media.

4. A system according to claim 3, wherein said media is either a paper or a polymer.

5. A system according to claim 1, wherein said minimum concentration of the vaporized hydrogen peroxide is at least 500 to 1500 ppm.

6. A system according to claim 1, wherein said system includes N of said indicator panels, each of the N said indicator panels undergoing a single permanent color change after exposure to said minimum concentration of vaporized hydrogen peroxide for N $\Delta t$ minutes.

7. In an apparatus having a chamber for decontaminating articles by exposing said articles to vaporized hydrogen peroxide (VHP), a method for visually verifying a minimum concentration of vaporized hydrogen peroxide (VHP) in said chamber, said method comprising:

introducing vaporized hydrogen peroxide into said chamber; and exposing a plurality of indicator panels to a concentration of vaporized hydrogen peroxide, each of said plurality of indicator panels having a chemistry thereon comprising iodide and thiosulfate, wherein the amount of thiosulfate on each said indicator panels is different to provide a different reaction time with the vaporized hydrogen peroxide:

each of said plurality of indicator panels undergoing a single permanent color change after a different exposure time to a minimum concentration of vaporized hydrogen peroxide, said single permanent color change produced by depletion of the thiosulfate and accumulation of triodide ions.

8. A method according to claim 7, wherein said iodide-based chemistry includes an iodide ion (I–), a thiosulfate ($S_2O_3^{2-}$) ion and starch.

9. A method according to claim 7, wherein said chemistry is coated onto a media.

10. A method according to claim 9, wherein said media is either a paper or a polymer.

11. A method according to claim 7, wherein said minimum concentration of the vaporized hydrogen peroxide is at least 500 to 1500 ppm.

12. A method according to claim 7, wherein said indicator has N of said indicator panels, each of the N said indicator panels undergoing a single permanent color change after exposure to said minimum concentration of vaporized hydrogen peroxide for N $\Delta t$ minutes.

13. An indicator for insuring that a minimum concentration of hydrogen peroxide is maintained in a decontamination chamber during a decontamination cycle, said indicator comprised of:
a carrier strip having a plurality of discrete sections thereon, said sections comprised of a chemistry reactive with vaporized hydrogen peroxide and each of said sections having a different amount of said chemistry, wherein each said section will undergo a single permanent color change when exposed to said minimum concentration of vaporized hydrogen peroxide for a respective select portion of said decontamination cycle.

14. An indicator according to claim 13, wherein said chemistry includes iodide and thiosulfate, said single permanent color change produced by depletion of the thiosulfate and accumulation of triodide ions.

15. An indicator according to claim 14, wherein said chemistry further includes starch.

* * * * *